(12) United States Patent
Kubanek et al.

(10) Patent No.: US 7,919,655 B2
(45) Date of Patent: Apr. 5, 2011

(54) METHOD FOR PRODUCING AN AMINE

(75) Inventors: Petr Kubanek, Mannheim (DE); Bram Willem Hoffer, Heidelberg (DE); Ekkehard Schwab, Neustadt (DE); Johann-Peter Melder, Böhl-Iggelheim (DE); Holger Evers, München (DE); Till Gerlach, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 118 days.

(21) Appl. No.: 12/373,849

(22) PCT Filed: Jul. 4, 2007

(86) PCT No.: PCT/EP2007/056724
§ 371 (c)(1),
(2), (4) Date: Jan. 14, 2009

(87) PCT Pub. No.: WO2008/006749
PCT Pub. Date: Jan. 17, 2008

(65) Prior Publication Data
US 2010/0010264 A1 Jan. 14, 2010

(51) Int. Cl.
C07C 209/16 (2006.01)
C07C 209/18 (2006.01)
C07C 209/26 (2006.01)
B01J 23/72 (2006.01)

(52) U.S. Cl. ........................................ 564/480; 502/331

(58) Field of Classification Search ........................ None
See application file for complete search history.

(56) References Cited

U.S. PATENT DOCUMENTS

| | | | |
|---|---|---|---|
| 3,275,554 A | 9/1966 | Wagenaar | |
| 3,751,475 A | 8/1973 | van der Voort et al. | |
| 4,152,353 A | 5/1979 | Habermann | |
| 4,153,581 A | 5/1979 | Habermann | |
| 4,832,702 A | 5/1989 | Kummer et al. | |
| 5,002,922 A | 3/1991 | Irgang et al. | |
| 5,530,127 A | 6/1996 | Reif et al. | |
| 5,608,113 A | 3/1997 | Becker et al. | |
| 6,057,442 A | 5/2000 | Wulff-Döring et al. | |
| 6,417,353 B1 | 7/2002 | Funke et al. | |
| 6,525,222 B2 | 2/2003 | Nouwen et al. | |
| 6,821,396 B2 | 11/2004 | Wolfert et al. | |
| 6,986,833 B2 | 1/2006 | Wölfert et al. | |
| 7,034,186 B2 | 4/2006 | Gerlach et al. | |
| 7,183,438 B2 | 2/2007 | Gerlach et al. | |
| 2008/0146846 A1 | 6/2008 | Dialer et al. | |
| 2008/0255351 A1 | 10/2008 | Hoffer et al. | |
| 2009/0264652 A1 | 10/2009 | Kubanek et al. | |
| 2009/0275781 A1 | 11/2009 | Kubanek et al. | |
| 2009/0286977 A1 | 11/2009 | Kubanek et al. | |
| 2009/0312579 A1 | 12/2009 | Kubanek et al. | |

FOREIGN PATENT DOCUMENTS

| | | |
|---|---|---|
| DE | 2125039 | 12/1971 |
| DE | 3611230 A1 | 10/1987 |
| DE | 102004062253 A1 | 7/2006 |
| EP | 0382049 A1 | 8/1990 |
| EP | 0514692 A2 | 11/1992 |
| EP | 0696572 A1 | 2/1996 |
| EP | 0697395 A2 | 2/1996 |
| EP | 0878462 A1 | 11/1998 |
| EP | 0905122 A2 | 3/1999 |
| EP | 0963975 A1 | 12/1999 |
| EP | 1035106 A1 | 9/2000 |
| EP | 1106600 A2 | 6/2001 |
| EP | 1312599 A1 | 5/2003 |
| EP | 1312600 A1 | 5/2003 |
| EP | 1431271 A1 | 6/2004 |
| WO | WO-00/69804 A1 | 11/2000 |
| WO | WO-03/051508 A1 | 6/2003 |
| WO | WO-03/076386 A2 | 9/2003 |
| WO | WO-2007/036496 A1 | 4/2007 |
| WO | WO-2008/006748 A1 | 1/2008 |
| WO | WO-2008/006749 A1 | 1/2008 |
| WO | WO-2008/006750 A1 | 1/2008 |
| WO | WO-2008/006752 A1 | 1/2008 |
| WO | WO-2008/006754 A1 | 1/2008 |

*Primary Examiner* — Brian J Davis
(74) *Attorney, Agent, or Firm* — Connolly Bove Lodge & Hutz LLP

(57) ABSTRACT

Processes comprising: (i) providing a reactant selected from the group consisting of primary alcohols, secondary alcohols, aldehydes, ketones and mixtures thereof; and (ii) reacting the reactant with hydrogen and a nitrogen compound selected from the group consisting of ammonia, primary amines, secondary amines and mixtures thereof, in the presence of a catalyst comprising a zirconium dioxide- and nickel-containing catalytically active composition, to form an amine; wherein the catalytically active composition, prior to reduction with hydrogen, comprises oxygen compounds of zirconium, copper, and nickel, and one or more oxygen compounds of one or more metals selected from the group consisting of Sb, Pb, Bi, and In.

33 Claims, No Drawings

METHOD FOR PRODUCING AN AMINE

CROSS-REFERENCE TO RELATED APPLICATIONS

This application is a national stage application, under 35 U.S.C. §371, of PCT/EP2007/056724 filed Jul. 4, 2007, which claims benefit of European Patent Application No. 06117259.9 filed Jul. 14, 2006.

BACKGROUND OF THE INVENTION

The process products find use, inter alia, as intermediates in the preparation of fuel additives (U.S. Pat. No. 3,275,554; DE-A-21 25 039 and DE-A-36 11 230), surfactants, medicaments and crop protectants, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

U.S. Pat. No. 4,153,581 (Habermann) relates to the amination of alcohols, aldehydes or ketones by means of specific Co/Cu catalysts which comprise Fe, Zn and/or Zr.

U.S. Pat. No. 4,152,353 (Dow) relates to the amination of alcohols, aldehydes or ketones by means of specific Ni/Cu catalysts, which comprise Fe, Zn and/or Zr.

EP-A1-382 049 (BASF AG) discloses catalysts which comprise oxygen-containing zirconium, copper, cobalt and nickel compounds, and processes for the hydrogenating amination of alcohols. The preferred zirconium oxide content of these catalysts is from 70 to 80% by weight (loc. cit.: page 2, last paragraph; page 3, 3rd paragraph; examples). Although these catalysts feature good activity and selectivity, they exhibit lifetimes in need of improvement.

EP-A2-514 692 (BASF AG) discloses catalysts comprising copper oxide, nickel oxide, and/or cobalt oxide, zirconium oxide and/or aluminum oxide for the catalytic amination of alcohols in the gas phase with ammonia or primary amines and hydrogen. This patent application teaches that the atomic ratio of nickel to copper in these catalysts must be from 0.1 to 1.0, preferably from 0.2 to 0.5 (cf. loc. cit.: Example 1), since yield-reducing by-products otherwise occur to an increased degree in the amination of alcohols (loc. cit.: Examples 6 and 12). The support used is preferably aluminum oxide (loc. cit., Examples 1 to 5 and 7 to 11).

EP-A1-696 572 and EP-A-697 395 (both BASF AG) disclose catalysts comprising nickel oxide, copper oxide, zirconium oxide and molybdenum oxide for the catalytic amination of alcohols with nitrogen compounds and hydrogen. Although these catalysts achieve high conversions, they can form by-products which themselves or whose conversion products are troublesome in the workup.

EP-A2-905 122 (BASF AG) describes a process for preparing amines from alcohols and nitrogen compounds using a catalyst whose catalytically active composition comprises oxygen compounds of zirconium, copper and nickel, and no oxygen compounds of cobalt or molybdenum.

EP-A-1 035 106 (BASF AG) relates to the use of catalysts comprising oxygen compounds of zirconium, copper and nickel for preparing amines by aminating hydrogenation of aldehydes or ketones.

EP-A1-963 975 and EP-A2-1 106 600 (both BASF AG) describe processes for preparing amines from, respectively, alcohols and aldehydes or ketones, and nitrogen compounds using a catalyst whose catalytically active composition comprises 22-40% by weight (or 22-45% by weight) of oxygen compounds of zirconium, 1-30% by weight of oxygen compounds of copper and in each case 15-50% by weight (or 5-50% by weight) of oxygen compounds of nickel and cobalt.

WO-A-03/076386 and EP-A1-1 431 271 (both BASF AG) also teach catalysts of the abovementioned type for aminations.

WO-A1-031051508 (Huntsman Petrochemical Corp.) relates to processes for aminating alcohols using specific Cu/Ni/Zr/Sn catalysts which, in a further embodiment, comprise Cr in place of Zr (see page 4, lines 10-16).

European patent application No. 06101339.7 of Feb. 6, 2006 (BASF AG) describes a process for preparing aminodiglycol (ADG) and morpholine by reacting diethylene glycol (DEG) with ammonia in the presence of a heterogeneous transition metal catalyst, the catalytically active composition of the catalyst, before the treatment with hydrogen, comprising oxygen compounds of aluminum and/or zirconium, copper, nickel and cobalt, and the shaped catalyst body having specific dimensions.

Four parallel European patent applications with the same filing date (all BASF AG) relate to particular doped zirconium dioxide-, copper- and nickel-containing catalysts and to their use in processes for preparing an amine by reacting a primary or secondary alcohol, aldehyde and/or ketone with hydrogen and ammonia, a primary or secondary amine.

When the very active catalysts of the prior art are used, including in particular the catalysts according to EP-A1-696 572, EP-A1-963 975 and EP-A2-1 106 600 (see above), there may be an increased tendency to decarbonylation of the carbonyl function (which may have formed as an intermediate) at elevated temperature in the reactants (alcohols, aldehyde, ketone). The formation of methane by hydrogenation of carbon monoxide (CO) leads, owing to the large amount of heat of hydrogenation released, to a "runaway risk", i.e. an uncontrolled temperature rise in the reactor. When CO is scavenged by amines, methyl-containing secondary components are formed.

In the amination of diethylene glycol (DEG), there is, for example, an increased tendency to form undesired methoxyethanol or methoxyethylamine.

In the case of the example of the amination of diethylene glycol (DEG), the "decarbonylation" is viewed in particular as the sum of undesired components (methanol, methoxyethanol, methoxyethylamine, N-methyl morpholine and methoxy-ethylmorpholine) which are formed from DEG via methoxyethanol according to the reaction network:

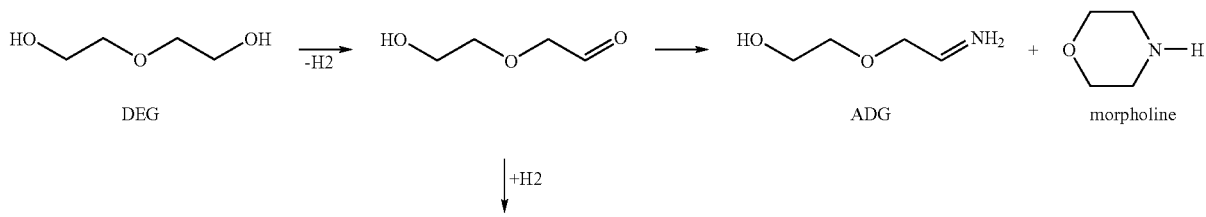

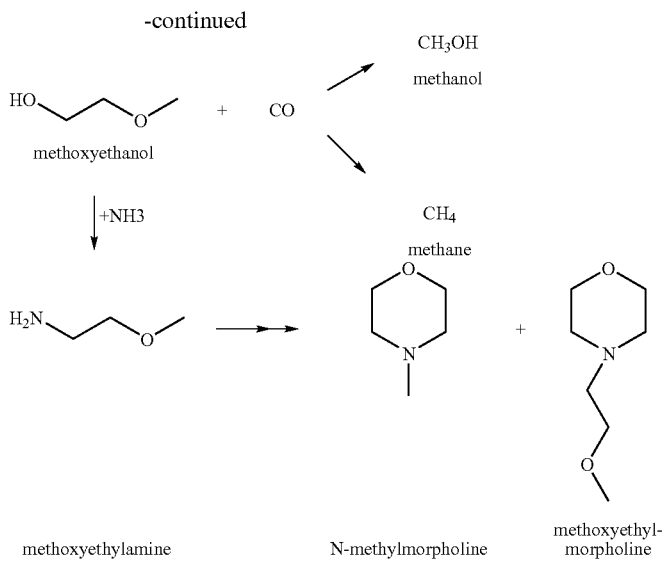

The reaction mechanism of the amination of primary or secondary alcohols is assumed to be that the alcohol is initially dehydrogenated to the corresponding aldehyde at a metal site. In this reaction, the copper is suspected to be of particular significance as a dehydrogenation component. When aldehydes are used for the amination, this step is not needed.

The aldehyde formed or used can be aminated by reaction with ammonia or primary or secondary amine with elimination of water and subsequent hydrogenation. This condensation of the aldehyde with the abovementioned nitrogen compound is suspected to be catalyzed by acidic sites of the catalyst. In an undesired side reaction, the aldehyde can also be decarbonylated, i.e. in that the aldehyde function is eliminated as CO. The decarbonylation or methanization is suspected to take place at a metallic site. The CO is hydrogenated to methane over the hydrogenation catalyst, so that the methane formation indicates the extent of decarbonylation. The decarbonylation forms the abovementioned undesired by-products, for example methoxyethanol and/or methoxyethylamine in the abovementioned case.

The desired condensation of the aldehyde with ammonia or primary or secondary amine and the undesired decarbonylation of the aldehyde are parallel reactions, of which the desired condensation is suspected to be acid-catalyzed, while the undesired decarbonylation is catalyzed by metallic sites.

BRIEF SUMMARY OF THE INVENTION

The present invention relates to zirconium dioxide- and nickel-containing catalysts and to a process for preparing an amine by reacting a primary or secondary alcohol, aldehyde and/or ketone with hydrogen and a nitrogen compound selected from the group of ammonia, primary and secondary amines, in the presence of a zirconium dioxide- and nickel-containing catalyst.

It was an object of the present invention to improve the economic viability of existing processes for hydrogenating amination of aldehydes or ketones and the amination of alcohols, and to remedy one or more disadvantages of the prior art, especially the abovementioned disadvantages. The intention was to find catalysts which can be prepared industrially in a simple manner and which enable the above-mentioned aminations to be performed with high conversion, high yield, space-time yields (STY), selectivity, catalyst lifetime with simultaneously high mechanical stability of the shaped catalyst body and low "runaway risk". The catalysts should accordingly have a high activity and have high chemical and mechanical stability under the reaction conditions.

[Space-time yields are reported in "amount of product/(catalyst volume·time)" (kg/($l_{cat}$·h)) and/or "amount of product/(reactor volume·time)' (kg/($l_{reactor}$·h)].

Accordingly, we have found a process for preparing an amine by reacting a primary or secondary alcohol, aldehyde and/or ketone with hydrogen and a nitrogen compound selected from the group of ammonia, primary and secondary amines, in the presence of a zirconium dioxide- and nickel-containing catalyst, wherein the catalytically active composition of the catalyst, before its reduction with hydrogen, comprises oxygen compounds of zirconium, copper and nickel, and oxygen compounds of one or more metals selected from Sb, Pb, Bi and In.

We have also found catalysts which comprise oxygen compounds of zirconium, copper and nickel, and oxygen compounds of one or more metals selected from Sb, Pb, Bi and In.

More particularly, we have found catalysts whose catalytically active composition, before their reduction with hydrogen, comprises in the range from 10 to 75% by weight of oxygen compounds of zirconium, calculated as $ZrO_2$, 1 to 30% by weight of oxygen compounds of copper, calculated as CuO, 10 to 70% by weight of oxygen compounds of nickel, calculated as NiO, and 0.1 to 10% by weight of oxygen compounds of one or more metals selected from Sb, Pb, Bi and In, calculated in each case as $Sb_2O_3$, PbO, $Bi_2O_3$ and $In_2O_3$ respectively, and their use in the abovementioned amination process, especially in the process for reacting DEG with ammonia.

In accordance with the invention, it has been recognized that the activity of the catalyst for the amination of primary or secondary alcohols, aldehydes and/or ketones in the presence of $H_2$, for example the amination of diethylene glycol (DEG) with ammonia to give aminodiglycol and morpholine, as a result of the additional content in the zirconium-copper-nickel catalysts of Sb, Pb, Bi and/or In, essentially at least remains constant, but the extent of the undesired decarbonylation reaction simultaneously decreases and hence the selectivity of the amination reaction increases.

The process can be performed continuously or batchwise. Preference is given to a continuous method.

DETAILED DESCRIPTION OF THE INVENTION

For the synthesis in the gas phase, the reactants are fed to the reactor in a controlled manner, preferably in a cycle gas stream, evaporated and in gaseous form. Suitable amines for a gas phase synthesis are amines which, owing to their boiling points and the boiling points of their reactants, can be kept in the gas phase within the process parameters by process technology means. The cycle gas serves firstly to evaporate the reactants and secondly as a reactant for the amination.

In the cycle gas method, the starting materials (alcohol, aldehyde and/or ketone, hydrogen and the nitrogen compound) are evaporated in a cycle gas stream and fed to the reactor in gaseous form.

The reactants (alcohol, aldehyde and/or ketone, the nitrogen compound) may also be evaporated as aqueous solutions and passed to the catalyst bed with the cycle gas stream.

Preferred reactors are tubular reactors. Examples of suitable reactors with cycle gas stream can be found in Ullmann's Encyclopedia of Industrial Chemistry, 5th Ed., Vol, B 4, pages 199-238, "Fixed-Bed Reactors".

Alternatively, the reaction is advantageously effected in a tube bundle reactor or in a single-stream plant.

In a single-stream plant, the tubular reactor in which the reaction proceeds can consist of a series connection of a plurality of (e.g. two or three) individual tubular reactors. Optionally, an intermediate introduction of feed (comprising the reactant and/or ammonia and/or $H_2$) and/or cycle gas and/or reactor effluent from a downstream reactor is possible here in an advantageous manner.

The cycle gas flow rate is preferably in the range from 40 to 1500 $m^3$ (at operating pressure)/[$m^3$ of catalyst (bed volume) ·h], in particular in the range from 100 to 700 $m^3$ (at operating pressure)/[$m^3$ of catalyst (bed volume)·h].

The cycle gas comprises preferably at least 10% by volume, particularly from 50 to 100% by volume, very particularly from 80 to 100% by volume of $H_2$.

For the synthesis in the liquid phase, suitable reactants and products are all of those which have high boiling points or are thermally labile. In these cases, a further advantage is that it is possible to dispense with evaporation and recondensation of the amine in the process.

In the process according to the invention, the catalysts are preferably used in the form of catalysts which consist only of catalytically active composition and, if appropriate, a shaping assistant (for example graphite or stearic acid) if the catalyst is used as a shaped body, i.e. do not comprise any further catalytically active ingredients. In this connection, the oxidic support material zirconium dioxide ($ZrO_2$) is considered to be included in the catalytically active composition.

The catalysts are used in such a way that the catalytically active composition ground to powder is introduced into the reaction vessel or that the catalytically active composition, after grinding, mixing with shaping assistants, shaping and heat treatment, is arranged in the reactor as shaped catalyst bodies—for example as tablets, spheres, rings, extrudates (e.g. strands).

The concentration data (in % by weight) of the components of the catalyst are based in each case, unless stated otherwise, on the catalytically active composition of the finished catalyst after its last heat treatment and before its reduction with hydrogen.

The catalytically active composition of the catalyst, after its last heat treatment and before its reduction with hydrogen, is defined as the sum of the masses of the catalytically active constituents and of the abovementioned catalyst support materials, and comprises essentially the following constituents:

zirconium dioxide ($ZrO_2$), oxygen compounds of copper and nickel and oxygen compounds of the metals Sb, Pb, Bi and In.

The sum of the abovementioned constituents of the catalytically active composition is typically from 70 to 100% by weight, preferably from 80 to 100% by weight, more preferably from 90 to 100% by weight, particularly >95% by weight, very particularly >98% by weight, in particular >99% by weight, for example more preferably 100% by weight.

The catalytically active composition of the inventive catalysts and those used in the process according to the invention may also comprise one or more elements (oxidation stage 0) or their inorganic or organic compounds selected from groups I A to VI A and I B to VII B and VIII of the Periodic Table of the Elements.

Examples of such elements and their compounds are: transition metals such as Re or rhenium oxides, Mn or $MnO_2$, W or tungsten oxides, Ta or tantalum oxides, Nb or niobium oxides or niobium oxalate, V or vanadium oxides or vanadyl pyrophosphate; lanthanides such as Ce or $CeO_2$, or Pr or $Pr_2O_3$; alkali metal oxides such as $Na_2O$; alkali metal carbonates such as $Na_2CO_3$; alkaline earth metal oxides such as SrO; alkaline earth metal carbonates such as $MgCO_{31}$ $CaCO_3$ and $BaCO_3$; boron oxide ($B_2O_3$).

The catalytically active composition of the inventive catalysts and those used in the process according to the invention preferably does not comprise any cobalt, more preferably does not comprise any cobalt, any ruthenium, any iron and/or any zinc.

The catalytically active composition of the catalyst, before its reduction with hydrogen comprises, preferably in the range from 0.1 to 10% by weight, particularly in the range from 0.2 to 7% by weight, more particularly in the range from 0.4 to 5% by weight, very particularly in the range from 2 to 4.5% by weight, of oxygen compounds of one or more metals selected from Sb, Pb, Bi and In, calculated in each case as $Sb_2O_3$, PbO, $Bi_2O_3$ and $In_2O_3$ respectively.

The metal is more preferably selected from Sb and In.

In addition, the catalytically active composition of the catalyst, before its reduction with hydrogen, comprises preferably in the range from 10 to 75% by weight, particularly from 25 to 65% by weight, more particularly from 30 to 55% by weight, of oxygen compounds of zirconium, calculated as $ZrO_2$, 1 to 30% by weight, particularly from 2 to 25% by weight, more particularly from 5 to 15%, by weight of oxygen compounds of copper, calculated as CuO, and 10 to 70% by weight, particularly from 20 to 60% by weight, more particularly from 30 to 50% by weight, of oxygen compounds of nickel, calculated as NiO.

The molar ratio of nickel to copper is preferably greater than 1, more preferably greater than 1.2, even more preferably in the range from 1.8 to 8.5.

To prepare the catalysts used in the process according to the invention, various processes are possible. They are, for example, obtainable by peptizing pulverulent mixtures of the hydroxides, carbonates, oxides and/or other salts of the components with water and subsequently extruding and heat-treating the composition thus obtained.

Preference is given to preparing the inventive catalysts by employing precipitation methods. For example, they can be obtained by coprecipitating the nickel, copper and doping metal components from an aqueous salt solution comprising these elements by means of bases in the presence of a slurry of a sparingly soluble, oxygen-containing zirconium compound and subsequently washing, drying and calcining the resulting precipitate. The sparingly soluble oxygen-containing zirconium compounds used may, for example, be zirconium dioxide, zirconium oxide hydrate, zirconium phosphates, zirconium borates and zirconium silicates. The slurries of the sparingly soluble zirconium compounds can be prepared by suspending fine powders of these compounds in water with vigorous stirring. Advantageously, these slurries are obtained by precipitating the sparingly soluble zirconium compounds from aqueous zirconium salt solutions by means of bases.

The inventive catalysts are preferably prepared by means of a coprecipitation (mixed precipitation) of all of their components. To this end, an aqueous salt solution comprising the catalyst components is appropriately admixed with an aqueous base—for example sodium carbonate, sodium hydroxide, potassium carbonate or potassium hydroxide—under hot conditions with stirring until the precipitation is complete. It is also possible to work with alkali metal-free bases such as ammonia, ammonium carbonate, ammonium hydrogencarbonate, ammonium carbamate, ammonium oxalate, ammonium malonate, urotropin, urea, etc. The type of salts used is generally not critical: since the principal factor in this procedure is the water solubility of the salts, a criterion is their good water solubility required to prepare these comparatively highly concentrated salt solutions. It is considered to be self-evident that, when selecting the salts of the individual components, the salts selected will of course only be those with anions which do not lead to disruption, whether by causing undesired precipitations or by complicating or preventing the precipitation by complex formation.

The precipitates obtained in these precipitation reactions are generally chemically inhomogeneous and consist, inter alia, of mixtures of the oxides, oxide hydrates, hydroxides, carbonates and insoluble and basic salts of the metals used. It may be found to be favorable for the filterability of the precipitates when they are aged, i.e. when they are left for a certain time after the precipitation, if appropriate under hot conditions or while passing air through.

The precipitates obtained by these precipitation processes are processed further as usual to give the inventive catalysts. First, the precipitates are washed. The content of alkali metal which has been supplied by the (mineral) base which may have been used as a precipitant can be influenced via the duration of the washing operation and via the temperature and amount of the washing water. In general, prolonging the washing time or increasing the temperature of the washing water will decrease the content of alkali metal. After the washing, the precipitated material is generally dried at from 80 to 200° C., preferably at from 100 to 150° C., and then calcined. The calcination is performed generally at temperatures between 300 and 800° C., preferably at from 400 to 600° C., in particular at from 450 to 550° C.

The inventive catalysts may also be prepared by impregnating zirconium dioxide ($ZrO_2$) which is present, for example, in the form of powder or shaped bodies such as extrudates, tablets, spheres or rings.

The zirconium dioxide is used, for example, in the monoclinic or tetragonal form, preferably in the monoclinic form.

Shaped bodies can be produced by the customary processes.

The impregnation is likewise effected by the customary processes, as described, for example, in A. B. Stiles, Catalyst Manufacture—Laboratory and Commercial Preparations, Marcel Dekker, New York (1983), by applying an appropriate metal salt solution in each case in one or more impregnation stages, the metal salts used being, for example, appropriate nitrates, acetates or chlorides. After the impregnation, the composition is dried and optionally calcined.

The impregnation can be effected by the so-called incipient wetness method, in which the zirconium dioxide is moistened, in accordance with its water uptake capacity, up to a maximum of saturation with the impregnation solution. The impregnation can also be effected in supernatant solution.

In the case of multistage impregnation processes, it is appropriate to dry and optionally to calcine between individual impregnation steps. Multistage impregnation can be employed particularly advantageously when the zirconium dioxide is to be loaded with a relatively large amount of metal.

To apply the metal components to the zirconium dioxide, the impregnation can be effected simultaneously with all metal salts or successively in any sequence of the individual metal salts.

Subsequently, the catalysts prepared by impregnation are dried and preferably also calcined, for example within the calcination temperature ranges already specified above:

After the calcination, the catalyst is appropriately conditioned, whether it be by grinding to a certain particle size or by mixing it, after it has been ground, with shaping assistants such as graphite or stearic acid, compressing it by means of a press to moldings, for example tablets, and heat-treating. The heat treatment temperatures correspond preferably to the temperatures in the calcining.

The catalysts prepared in this way comprise the catalytically active metals in the form of a mixture of their oxygen compounds, i.e. in particular in the form of oxides and mixed oxides.

The catalysts prepared, for example, as described above are stored as such and, if appropriate, treated. Before they are used as catalysts, they are typically prereduced. However, they can also be used without prereduction, in which case they are reduced under the conditions of the hydrogenating amination by the hydrogen present in the reactor.

For prereduction, the catalysts are exposed to a nitrogen-hydrogen atmosphere first at preferably from 150 to 200° C. over a period of, for example, from 12 to 20 hours, and then treated in a hydrogen atmosphere at preferably from 200 to 400° C. for another up to approx. 24 hours. This prereduction reduces a portion of the oxygen-containing metal compounds present in the catalysts to the corresponding metals, so that they are present together with the different types of oxygen compounds in the active form of the catalyst.

A further advantage of the inventive catalysts is their mechanical stability, i.e. their hardness. The mechanical stability can be determined by the measurement of the so-called side crushing strength. For this purpose, the shaped catalyst body, for example the catalyst tablet, is stressed with increasing force between two parallel plates until fracture of the shaped catalyst body occurs, and this stress may act, for example, on the cylindrical surface of catalyst tablets. The force registered when the shaped catalyst body fractures is the side crushing strength.

The process according to the invention is preferably performed continuously, the catalyst preferably being arranged in the reactor as a fixed bed. It is possible for the flow toward the fixed catalyst bed to be either from the top or from the bottom. The gas stream is adjusted in terms of temperature, pressure and flow rate in such a way that even relatively high-boiling reaction products remain in the gas phase.

The aminating agent may, with regard to the alcoholic hydroxyl group or aldehyde group or keto group to be aminated, be used in stoichiometric, sub- or superstoichiometric amounts.

In the case of the amination of alcohols, aldehydes or ketones with primary or secondary amines, the amine is preferably used in an approximately stoichiometric amount or slightly superstoichiometric amount per mole of alcoholic hydroxyl group, aldehyde group or keto group to be aminated.

The amine component (nitrogen compound) is used preferably in from 0.90 to 100 times the molar amount, especially in from 1.0 to 10 times the molar amount, based in each case on the alcohol, aldehyde and/or ketone used.

Especially ammonia is used generally with a from 1.5- to 250-fold, preferably from 2- to 100-fold, especially from 2- to 10-fold molar excess per mole of alcoholic hydroxyl group, aldehyde group or keto group to be converted.

Higher excesses both of ammonia and of primary or secondary amines are possible.

Preference is given to employing an offgas flow rate of from 5 to 800 standard cubic meters/h, especially from 20 to 300 standard cubic meters/h.

The amination of the primary or secondary alcohol groups, aldehyde groups or keto groups of the reactant can be performed in the liquid phase or in the gas phase. Preference is given to the fixed bed process in the gas phase.

When working in the liquid phase, the reactants (alcohol, aldehyde or ketone plus ammonia or amine) are passed simultaneously, including hydrogen, over the catalyst, which is typically disposed in a fixed bed reactor preferably heated externally, in the liquid phase at pressures of generally from 5 to 30 MPa (50-300 bar), preferably from 5 to 25 MPa, more preferably from 15 to 25 MPa, and temperatures of generally from 80 to 350° C., particularly from 100 to 300° C., preferably from 120 to 270° C., more preferably from 130 to 250° C., in particular from 170 to 230° C. Both a trickle mode and a liquid-phase mode are possible. The catalyst hourly space velocity is generally in the range from 0.05 to 5 kg, preferably from 0.1 to 2 kg and more preferably from 0.2 to 0.6 kg of alcohol, aldehyde or ketone per liter of catalyst (bed volume) and hour. If appropriate, the reactants can be diluted with a suitable solvent such as tetrahydrofuran, dioxane, N-methylpyrrolidone or ethylene glycol dimethyl ether. It is appropriate to heat the reactants before they are fed into the reaction vessel, preferably to the reaction temperature.

When working in the gas phase, the gaseous reactants (alcohol, aldehyde or ketone plus ammonia or amine) are passed over the catalyst in the presence of hydrogen in a gas stream, preferably hydrogen, selected so as to be sufficiently large for evaporation, at pressures of generally from 0.1 to 40 MPa (from 1 to 400 bar), preferably from 0.1 to 10 MPa, more preferably from 0.1 to 5 MPa. The temperatures for the amination of alcohols are generally from 80 to 350° C., particularly from 100 to 300° C., preferably from 120 to 270° C., more preferably from 160 to 250° C. The reaction temperatures in the hydrogenating amination of aldehydes and ketones are generally from 80 to 350° C., particularly from 90 to 300° C., preferably from 100 to 250° C. The flow to the fixed catalyst bed may be either from above or from below. The required gas stream is preferably obtained by a cycle gas method.

The catalyst hourly space velocity is generally in the range from 0.01 to 2 and preferably from 0.05 to 0.5 kg of alcohol, aldehyde or ketone per liter of catalyst (bed volume) and hour.

The hydrogen is fed to the reaction generally in an amount of from 5 to 400 l, preferably in an amount of from 50 to 200 l per mole of alcohol, aldehyde or ketone component, the amounts in liters each having been converted to standard conditions (S.T.P.). The performance of the amination of aldehydes or ketones differs from that of the amination of alcohols in that at least stoichiometric amounts of hydrogen need to be present in the amination of aldehydes and ketones.

Both in the case of operation in the liquid phase and in the case of operation in the gas phase, it is possible to use higher temperatures and higher overall pressures and catalyst hourly space velocities. The pressure in the reaction vessel, which results from the sum of the partial pressures of the aminating agent, of the alcohol, aldehyde or ketone, and of the reaction products formed and, if appropriate, of the solvent used at the temperatures specified, is appropriately increased by injecting hydrogen up to the desired reaction pressure.

Both in the case of continuous operation in the liquid phase and in the case of continuous operation in the gas phase, the excess aminating agent can be circulated together with the hydrogen.

When the catalyst is arranged as a fixed bed, it may be advantageous for the selectivity of the reaction to mix the shaped catalyst bodies in the reactor with inert packings, to "dilute" them as it were. The proportion of packings in such catalyst preparations may be from 20 to 80 parts by volume, particularly from 30 to 60 parts by volume and in particular from 40 to 50 parts by volume.

The water of reaction formed in the course of the reaction (in each case one mole per mole of alcohol group, aldehyde group or keto group converted) generally does not have a disruptive effect on the degree of conversion, the reaction rate, the selectivity and the catalyst lifetime, and is therefore appropriately not removed therefrom until the workup of the reaction product, for example by distillation.

After the reaction effluent has appropriately been decompressed, the excess hydrogen and any excess aminating agent present are removed therefrom and the resulting crude reaction product is purified, for example by a fractional rectification. Suitable workup processes are described, for example, in EP-A-1 312 600 and EP-A-1 312 599 (both BASF AG). The excess aminating agent and the hydrogen are advantageously returned back into the reaction zone. The same applies to any incompletely converted alcohol, aldehyde or ketone component.

Unconverted reactants and any suitable by-products which are obtained can be returned back into the synthesis. Unconverted reactants can be flowed again in the cycle gas stream over the catalyst bed in batchwise or continuous mode after condensation of the products in the separator.

Aminating agents in the process according to the invention are, as well as ammonia, primary and secondary amines.

It is possible by the process according to the invention to prepare, for example, amines of the formula I

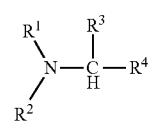

(I)

in which
R$^1$, R$^2$ are each hydrogen (H), alkyl such as C$_{1-20}$-alkyl, cycloalkyl such as C$_{3-12}$-cycloalkyl, alkoxyalkyl such as C$_{2-30}$-alkoxyalkyl, dialkylaminoalkyl such as C$_{3-30}$-dialkylaminoalkyl, aryl, aralkyl such as $C_{7-20}$-aralkyl and alkylaryl such as $C_{7-20}$-alkylaryl, or together are $-(CH_2)_j-X-(CH_2)_k-$, $R^3$, $R^4$ are each hydrogen (H), alkyl such as $C_{1-20}$-alkyl, cycloalkyl such as $C_{3-12}$-cycloalkyl, hydroxyalkyl such as $C_{1-20}$-hydroxyalkyl, aminoalkyl such as $C_{1-20}$-aminoalky), hydroxyalkylaminoalkyl such as $C_{2-20}$-hydroxyalkylaminoalkyl, alkoxyalkyl such as $C_{2-30}$ alkoxyalkyl, dialkylaminoalkyl such as $C_{3-30}$-dialkylamino-alkyl, alkylaminoalkyl such as $C_{2-30}$-alkylaminoalkyl, $R^5-(OCR^6R^7CR^8R^9)_n-(OCR^6R^7)$, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl, and $Y-(CH_2)_m-NR^5-(CH_2)_q$ or, together, $-(CH_2)_l-X-(CH_2)_m-$ or $R^2$ and $R^4$ together are $(CH_2)_l-X-(CH_2)_m-$, $R^5$, $R^{10}$ are each hydrogen (H), alkyl such as $C_{1-4}$-alkyl, alkylphenyl such as $C_{7-40}$-alkylphenyl, $R^6$, $R^7$, $R^8$, $R^9$ are each hydrogen (H), methyl or ethyl, X is $CH_2$, $CHR^5$, oxygen (O), sulfur (S) or $NR^5$, Y is $N(R^{10})_2$, hydroxyl, $C_{2-20}$-alkylaminoalkyl or $C_{3-20}$-dialkylaminoalkyl, n is an integer from 1 to 30 and j, k, l, m, q are each integers from 1 to 4.

The process according to the invention therefore preferably finds use for preparing an amine I by reacting a primary or secondary alcohol of the formula II

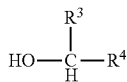

(II)

and/or an aldehyde and/or a ketone of the formula VI or VII

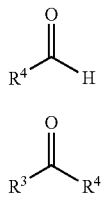

with a nitrogen compound of the formula III

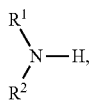

where $R^1$, $R^2$, $R^3$ and $R^4$ are each as defined above.

The reactant alcohol may also be an amino alcohol, for example an amino alcohol of the formula II.

As is evident from the definitions of the $R^2$ and $R^4$ radicals, the reaction can also be effected intramolecularly in an appropriate amino alcohol, amino ketone or amino aldehyde.

To prepare the amine 1, in a purely formal sense, a hydrogen atom of the nitrogen compound III is accordingly replaced by the $R^4(R^3)CH-$ radical with release of one molar equivalent of water.

The process according to the invention preferably also finds use in the preparation of a cyclic amine of the formula IV

in which $R^{11}$ and $R^{12}$ are each hydrogen (H), alkyl such as $C_1$- to $C_{20}$-alkyl, cycloalkyl such as $C_3$- to $C_{12}$-cycloalkyl, aryl, heteroaryl, aralkyl such as $C_7$- to $C_{20}$-aralkyl, and alkylaryl such as $C_7$- to $C_{20}$-alkylaryl, Z is $CH_2$, $CHR^5$, oxygen (O), $NR^5$ or $NCH_2CH_2OH$ and $R^1$, $R^6$, $R^7$ are each as defined above by reacting an alcohol of the formula V

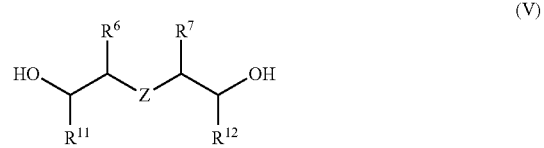

with ammonia or a primary amine of the formula VI

The substituents $R^1$ to $R^{12}$, the variables X, Y, Z, and the indices j, k, l, m, n and q in the compounds I, II, III, IV, V, VI and VII are each independently defined as follows:

$R^1$, $R^2$, $R^3$, $R^4$, $R^5$, $R^6$, $R^7$, $R^8$, $R^9$, $R^{10}$, $R^{11}$, $R^{12}$:
  hydrogen (H), $R^3$, $R^4$:
  alkyl such as $C_{1-20}$-alkyl, preferably $C_{1-14}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, hydroxyalkyl such as $C_{1-20}$-hydroxyalkyl, preferably $C_{1-8}$-hydroxyalkyl, more preferably $C_{1-4}$-hydroxyalkyl, such as hydroxymethyl, 1-hydroxyethyl, 2-hydroxy-ethyl, 1-hydroxy-n-propyl, 2-hydroxy-n-propyl, 3-hydroxy-n-propyl and 1-(hydroxy methyl)ethyl, aminoalkyl such as $C_{1-20}$-aminoalkyl, preferably $C_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl) aminomethyl, hydroxyalkylaminoalkyl such as $C_{2-20}$-hydroxyalkylaminoalkyl, preferably $C_{3-8}$-hydroxyalkylaminoalkyl, such as (2-hydroxyethylamino)methyl, 2-(2-hydroxyethylamino)ethyl and 3-(2-hydroxyethylamino)propyl, $R^5-(OCR^6R^7CR^8R^9)_n-(OCR^6R^7)$, preferably $R^5-(OCHR^7CHR^9)_n-(OCR^6R^7)$, more preferably $R^5-(OCH_2CHR^9)_n-(OCR^6R^7)$, alkylaminoalkyl such as $C_{2-30}$-alkylaminoalkyl, preferably $C_{2-20}$-alkylaminoalkyl, more preferably $C_{2-8}$-alkylaminoalkyl, such as methylaminomethyl, 2-methyl-aminoethyl, ethylaminomethyl, 2-ethylaminoethyl and 2-(isopropylamino)ethyl, $(R^5)HN—(CH_2)_q$,
$Y—(CH_2)_m—NR^5—(CH_2)_q$, heteroarylalkyl such as $C_{4-20}$-heteroarylalkyl, such as pyrid-2-ylmethyl, furan-2-ylmethyl, pyrrol-3-ylmethyl and imidazol-2-ylmethyl, alkylheteroaryl such as $C_{4-20}$-alkylheteroaryl, such as 2-methyl-3-pyridinyl, 4,5-di-methylimidazol-2-yl, 3-methyl-2-furanyl and 5-methyl-2-pyrazinyl, heteroaryl such as 2-pyridinyl, 3-pyridinyl, 4-pyridinyl, pyrazinyl, pyrrol-3-yl, imidazol-2-yl, 2-furanyl and 3-furanyl, $R^1$, $R^2$, $R^3$, $R^4$:

cycloalkyl such as $C_{3-12}$-cycloalkyl, preferably $C_{3-8}$-cycloalkyl, such as cyclopropyl, cyclobutyl, cyclopentyl, cyclohexyl, cycloheptyl and cyclooctyl, more preferably cyclopentyl and cyclohexyl, alkoxyalkyl such as $C_{2-30}$-alkoxyalkyl, preferably $C_{2-20}$-alkoxyalkyl, more preferably $C_{2-8}$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, more preferably $C_{2-4}$-alkoxyalkyl, dialkylaminoalkyl such as $C_{3-30}$-dialkylaminoalkyl, preferably $C_{3-20}$-dialkylamino-alkyl, more preferably $C_{3-10}$-dialkylaminoalkyl, such as N,N-dimethylaminomethyl, (N,N-dibutylamino)methyl, 2-(N,N-dimethylamino) ethyl, 2-(N,N-diethyl-amino)ethyl, 2-(N,N-dibutylamino)ethyl, 2-(N,N-di-n-propylamino)ethyl and 2-(N,N-diisopropylamino)ethyl, 3-(N,N-dimethylamino) propyl, $(R^5)_2N—(CH_2)_q$, aryl such as phenyl, 1-naphthyl, 2-naphthyl, 1-anthryl, 2-anthryl and 9-anthryl, preferably phenyl, 1-naphthyl and 2-naphthyl, more preferably phenyl, alkylaryl such as $C_{7-20}$-alkylaryl, preferably $C_{7-12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, aralkyl such as $C_{7-20}$-aralkyl, preferably $C_{7-12}$-phenylalkyl, such as benzyl, p-methoxybenzyl, 3,4-dimethoxybenzyl, 1-phenethyl, 2-phenethyl, 1-phenyl-propyl, 2-phenylpropyl, 3-phenylpropyl, 1-phenylbutyl, 2-phenylbutyl, 3-phenyl-butyl and 4-phenylbutyl, more preferably benzyl, 1-phenethyl and 2-phenethyl, $R^3$ and $R^4$ or $R^2$ and $R^4$ together are a $(CH_2)_j—X—(CH_2)_m$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR^5—(CH_2)_3—$, $R^1$, $R^2$:

alkyl such as $C_{1-20}$-alkyl, preferably $C_{1-8}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, more preferably $C_{1-4}$-alkyl, or $R^1$ and $R^2$ together are a $—(CH_2)_j—X—(CH_2)_k—$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR^5—(CH_2)_3—$, $R^5$, $R^{10}$:

alkyl, preferably $C_{1-4}$-alkyl, such as methyl, ethyl, n-propyl, isopropyl, n-butyl, isobutyl, sec-butyl and tert-butyl, preferably methyl and ethyl, more preferably methyl, alkylphenyl, preferably $C_{7-40}$-alkylphenyl, such as 2-methylphenyl, 3-methyl-phenyl, 4-methylphenyl, 2,4-dimethylphenyl, 2,5-dimethylphenyl, 2,6-dimethyl-phenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, in particular $C_{7-20}$-alkylphenyl, $R^6$, $R^7$, $R^8$, $R^9$:

methyl or ethyl, preferably methyl, $R^{11}$, $R^{12}$:

alkyl such as $C_1$- to $C_{20}$-alkyl, cycloalkyl such as $C_3$- to $C_{12}$-cycloalkyl, aryl, heteroaryl, aralkyl such as $C_7$- to $C_{20}$-aralkyl, and alkylaryl such as $C_7$- to $C_{20}$-alkylaryl, in each case as defined above,

X:

$CH_2$, $CHR^5$, oxygen (O), sulfur (S) or $NR^5$, preferably $CH_2$ and O,

Y:

$N(R^{10})_2$, preferably $NH_2$ and $N(CH_3)_2$, hydroxyl (OH), $C_{2-20}$-alkylaminoalkyl, preferably $C_{2-16}$-alkylaminoalkyl, such as methylamino-methyl, 2-methylaminoethyl, ethylaminomethyl, 2-ethylaminoethyl and 2-(iso-propylamino)ethyl, $C_{3-20}$-dialkylaminoalkyl, preferably $C_{3-16}$-dialkylaminoalkyl, such as dimethylamino-methyl, 2-dimethylaminoethyl, 2-diethylaminoethyl, 2-(di-n-propylamino)ethyl and 2-(diisopropylamino)ethyl,

Z:

$CH_2$, $CHR^5$, O, $NR^5$ or $NCH_2CH_2OH$, j, l:

an integer from 1 to 4 (1, 2, 3 or 4), preferably 2 and 3, more preferably 2, k, m, q:

an integer from 1 to 4 (1, 2, 3 or 4), preferably 2, 3 and 4, more preferably 2 and 3, n:

an integer from 1 to 30, preferably an integer from 1 to 8 (1, 2, 3, 4, 5, 6, 7 or 8), more preferably an integer from 1 to 6.

Suitable alcohols under the abovementioned prerequisites are virtually all primary and secondary alcohols with an aliphatic OH function. The alcohols may be straight-chain, branched or cyclic. Secondary alcohols are aminated just as efficiently as primary alcohols. The alcohols may also bear substituents or comprise functional groups which behave inertly under the conditions of the hydrogenating amination, for example alkoxy, alkenyloxy, alkylamino or dialkylamino groups, or else if appropriate are hydrogenated under the conditions of the hydrogenating amination, for example CC double or triple bonds. When polyhydric alcohols are to be aminated, it is possible via the control of the reaction conditions to obtain preferentially amino alcohols, cyclic amines or polyaminated products.

The amination of 1,4-diols leads, depending on the selection of the reaction conditions, to 1-amino-4-hydroxy compounds, 1,4-diamino compounds, or to five-membered rings with a nitrogen atom (pyrrolidines).

The amination of 1,6-diols leads, depending on the selection of the reaction conditions, to 1-amino-6-hydroxy compounds, 1,6-diamino compounds, or to seven-membered rings with a nitrogen atom (hexamethyleneimines).

The amination of 1,5-diols leads, depending on the selection of the reaction conditions, to 1-amino-5-hydroxy, 1,5-diamino compounds, or to six-membered rings with a nitrogen atom (piperidines, 1,5-dipiperidinylpentanes). It is accordingly possible to obtain from diglycol (DEG), by amination with $NH_3$, monoaminodiglycol (=ADG=$H_2N$—$CH_2CH_2$—O—$CH_2CH_2$—OH), diaminodiglycol ($H_2N$—$CH_2CH_2$—O—$CH_2CH_2$—$NH_2$) or more preferably morpholine piperazine is correspondingly obtained with particular preference from diethanolamine. N-(2-Hydroxyethyl) piperazine can be obtained from triethanolamine.

Preference is given to aminating, for example, the following alcohols:
methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)-ethanol, 2-(3,4-dimethoxyphenyl) ethanol, 1-phenyl-3-butanol, ethanolamine, n-propanolamine, isopropanolamine, 2-amino-1-propanol, 1-methoxy-2-propanol, 3-amino-2,2-dimethyl-1 propanol, n-pentanolamine (1-amino-5-pentanol), n-hexanol-amine (1-amino-6-hexanol), ethanolamine, diethanolamine, triethanolamine, N-alkyl-diethanolamines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino)ethanol, 2-(N,N-di-n-butylamino)ethanol, 2-(N,N-diisobutyl-amino) ethanol, 2-(N,N-di-sec-butylamino)ethanol, 2-(N,N-di-tert-butylamino)ethanol, 3-(N,N-dimethylamino)propanol, 3-(N, N-diethylamino)propanol, 3-(N,N-di-n-propylamino) propanol, 3-(N,N-diisopropylamino)propanol, 3-(N,N-di-n-butylamino)propanol, 3-(N,N-diisobutylamino)propanol, 3-(N,N-di-sec-butylamino)-propanol, 3-(N,N-di-tert-butylamino)propanol, 1-dimethylaminopentanol-4,1-di-ethylaminopentanol-4, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polypropyl alcohols, polyethylene glycol ethers, polypropylene glycol ethers and polybutylene glycol ethers. The latter polyalkylene glycol ethers are converted to the corresponding amines in the inventive reaction by converting their free hydroxyl groups.

Particularly preferred alcohols are methanol, ethanol, n-propanol, i-propanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-dimethylaminoethoxy)ethanol, N-methyldiethanolamine and 2-(2-di-methylaminoethoxy)ethanol.

Suitable ketones usable in the process according to the invention are, under the abovementioned prerequisites, virtually all aliphatic and aromatic ketones. The aliphatic ketones may be straight-chain, branched or cyclic; the ketones may comprise heteroatoms. The ketones may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds. When polyfunctional ketones are to be aminated, it is possible via the control of the reaction conditions to obtain amino ketones, amino alcohols, cyclic amines or polyaminated products.

Preference is given, for example, to aminatingly hydrogenating the following ketones:
acetone, ethyl methyl ketone, methyl vinyl ketone, isobutyl methyl ketone, butanone, 3-methylbutan-2-one, diethyl ketone, tetralone, acetophenone, p-methylacetophenone, p-methoxyacetophenone, m-methoxyacetophenone, 1-acetylnaphthalene, 2-acetyl-naphthalene, 1-phenyl-3-butanone, cyclobutanone, cyplopentanone, cyclopentenone, cyclohexanone, cyclohexenone, 2,6-dimethylcyclohexanone, cycloheptanone, cyclododecanone, acetylacetone, methylglyoxal and benzophenone.

Suitable aldehydes usable in the process according to the invention are, under the abovementioned prerequisites, virtually all aliphatic and aromatic aldehydes. The aliphatic aldehydes may be straight-chain, branched or cyclic; the aldehydes may comprise heteroatoms. The aldehydes may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds. When polyfunctional aldehydes or keto aldehydes are to be aminated, it is possible via the control of the reaction conditions to obtain amino alcohols, cyclic amines or polyaminated products.

Preference is given, for example, to aminatingly hydrogenating the following aldehydes:
formaldehyde, acetaldehyde, propionaldehyde, n-butyraldehyde, isobutyraldehyde, pivalaldehyde, n-pentanal, n-hexanal, 2-ethylhexanal, 2-methyl pentanal, 3-methyl-pentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, lysmeral, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and hydroformylated oligomers and polymers, for example hydroformylated polyisobutene (polyisobutenealdehyde) or hydroformylated oligomer obtained by metathesis of 1-pentene and cyclopentene.

The aminating agents used in the hydrogenating amination of alcohols, aldehydes or ketones in the presence of hydrogen may be either ammonia or primary or secondary, aliphatic or cycloaliphatic or aromatic amines.

When the aminating agent used is ammonia, the alcoholic hydroxyl group or the aldehyde group or the keto group is initially converted to the primary amino groups (—$NH_2$). The primary amine thus formed may react with further alcohol or aldehyde or ketone to give the corresponding secondary amine and this may in turn react with further alcohol or aldehyde or ketone to give the corresponding, preferably symmetrical, tertiary amine. Depending on the composition of the reaction mixture or of the reactant stream (in continuous mode), and depending on the reaction conditions employed—pressure, temperature, reaction time (catalyst hourly space velocity)—it is possible in this way to prepare preferentially primary, secondary or tertiary amines as desired.

In this way, it is possible to prepare, from polyhydric alcohols or di- or oligoaldehydes or di- or oligoketones or keto aldehydes, by intramolecular hydrogenating amination, cyclic amines, for example pyrrolidines, piperidines, hexamethyleneimines, piperazines and morpholines.

As well as ammonia, the aminating agents used may equally be primary or secondary amines.

These aminating agents are preferably used to prepare unsymmetrically substituted di- or trialkylamines, such as ethyldiisopropylamine and ethyldicyclohexylamine. For example the following mono- and dialkylamines are used as aminating agents: monomethylamine, dimethylamine, monoethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, 5-pentylamine, isopentylamine, n-hexylamine, s-hexylamine, iso-hexylamine, cyclohexylamine, aniline, toluidine, piperidine, morpholine and pyrrolidine.

Amines prepared with particular preference by the process according to the invention are, for example, morpholine (from monoaminodiglycol), monoaminodiglycol, morpholine and/or 2,2'-dimorpholinodiethyl ether (DMDEE) (from DEG and ammonia), 6-dimethylaminohexanol-1 (from hexanediol and dimethylamine (DMA)), triethylamine (from ethanol and diethylamine (DEA)), dimethylethylamine (from ethanol and DMA), N—($C_{1-4}$-alkyl)morpholine (from DEG and mono($C_{1-4}$-alkyl)amine), N—($C_{1-4}$-alkyl)piperidine (from 1,5-pentanediol and mono($C_{1-4}$-alkyl)amine), piperazine and/or diethylenetriamine (DETA) (from N-(2-aminoethyl)ethanolamine (AFEA) and ammonia), N-methylpiperazine (from diethanolamine and MMA), N,N'-dimethylpiperazine (from N-methyldiethanolamine and MMA), 1,2-ethylenediamine (EDA) and/or diethylenetriamine (DETA) and/or PIP (from monoethanolamine (MEOA) and ammonia), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino-4-aminopentane (from 1-diethylamino-4-hydroxypentane and $NH_3$), N,N-di($C_{1-4}$-alkyl)cyclohexylamine (from cyclohexanone and/or cyclohexanol and di($C_{1-4}$-alkyl)amine), e.g. N,N-dimethyl-N-cyclohexylamine (DMCHA), polyisobuteneamine (PIBA; where, for example, n~1000) (from polyisobutenaldehyde and $NH_3$), N,N-diisopropyl-N-ethylamine (Hünig's base) (from N,N-diisopropylamine and acetaldehyde), N-methyl-N-isopropylamine (MMIPA) (from monomethylamine and acetone), n-propylamines (such as mono-/di-n-propylamine, N,N-dimethyl-N-n-propylamine (DMPA)) (from propionaldehyde and/or n-propanol and $NH_3$ or DMA), N,N-dimethyl-N-isopropylamine (DMIPA) (from i-propanol and/or acetone and DMA), N,N-dimethyl-N-butylamines (1-, 2- or isobutanol and/or butanal, i-butanal or butanone and DMA), 2-(2-di($C_{1-4}$-alkyl)aminoethoxy)ethanol and/or bis(2-di($C_{1-4}$-alkyl)aminoethyl)ether (from DEG and di($C_{1-4}$-alkyl)amine), 1,2-ethylenediamine (EDA), monoethanolamine (MEOA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from triethylene glycol (TEG) and ammonia), 1-methoxy-2-propylamine (1-methoxyisopropylamine, MOIPA) (from 1-methoxy-2-propanol and ammonia), N-cyclododecyl-2,6-dimethylmorpholine (dodemorph) (from cyclododecanone and/or cyclododecanol and 2,6-dimethylmorpholine), polyetheramine (from corresponding polyether alcohol and ammonia). The polyether alcohols are, for example, polyethylene glycols or polypropylene glycols having a molecular weight in the range from 200 to 5000 g/mol; the corresponding polyetheramines are obtainable, for example, under the tradename PEA D230, D400; D2000, T403 or T5000 from BASF.

EXAMPLES

Example 1

Preparation of Amination Catalyst 1 (Based on Ni—Cu/$ZrO_2$=Comparative Experiment According to EP-A-697 395 and EP-A-696 572)

An aqueous solution of nickel nitrate, copper nitrate and zirconium acetate which comprises 4.48% by weight of Ni (calculated as NiO), 1.52% by weight of Cu (calculated as CuO) and 2.82% by weight of Zr (calculated as $ZrO_2$) was precipitated simultaneously in a stirred vessel in a constant stream with a 20% aqueous sodium carbonate solution at a temperature of 70° C. in such a way that the pH, measured with a glass electrode, of 7.0 was maintained. The resulting suspension was filtered and the filtercake was washed with demineralized water until the electrical conductivity of the filtrate was approx. 20 µS. Sufficient ammonium heptamolybdate was then incorporated into the still-moist filtercake that the oxide mixture specified below was obtained. Thereafter, the filtercake was dried at a temperature of 150° C. in a drying cabinet or a spray dryer. The hydroxide-carbonate mixture obtained in this way was then heat-treated at a temperature of from 450 to 500° C. over a period of 4 hours. The catalyst thus prepared had the composition: 50% by weight of NiO, 17% by weight of CuO, 1.5% by weight of $MoO_3$ and 31.5% by weight of $ZrO_2$. The catalyst was mixed with 3% by weight of graphite and shaped to tablets. The oxidic tablets were reduced. The reduction was performed at 280° C. at a heating rate of 3° C./minute. Reduction was effected first with 10% $H_2$ in $N_2$ for 50 minutes, then with 25% $H_2$ in $N_2$ for 20 minutes, then with 50% $H_2$ in $N_2$ for 10 minutes, then with 75% $H_2$ in $N_2$ for 10 minutes and finally with 100% $H_2$ for 3 hours. The percentages are each % by volume. The passivation of the reduced oxidic species was performed at room temperature in dilute air (air in $N_2$ with a maximum $O_2$ content of 5% by volume).

Example 2

The catalyst was prepared analogously to catalyst 1, except that indium nitrate was additionally added to the nitrate solution. Furthermore, addition of ammonium heptamolybdate was dispensed with. The catalyst 2 thus obtained had the composition as detailed in Table I.

Example 3

The catalyst was prepared analogously to catalyst 1, except that antimony oxide dissolved in concentrated aqueous KOH was additionally added to the 20% sodium carbonate solution. Furthermore, addition of ammonium heptamolybdate was dispensed with. The catalyst 3 thus obtained had the composition as detailed in Table I.

Example 4

Amination of Diethylene Glycol (DEG)

8 g of the reduced amination catalyst in the form of approx. 1 mm spall was initially charged in a 300 ml autoclave together with 80 g of diethylene glycol (0.75 mol). 34 g of liquid ammonia (2 mol) were added to the reaction mixture, and the autoclave was injected with hydrogen to 70 bar and heated to 200° C. At 200° C., hydrogen was again injected to 20 bar, and the total pressure rose to 180-200 bar. The autoclave was run at 200° C. for 12 hours with stirring.

At different times, samples of the reaction mixture were taken and analyzed by means of GC chromatography. For this purpose, a 30 m "RTX-5 amine" GC column was used, with a temperature program of: 80° C./15 minutes, heat to 290° C. within 30 minutes, at 290° C./15 minutes.

The composition of the resulting reaction mixtures for the catalysts of Examples 1 to 3 can be taken from Table I.

TABLE I

Doped catalysts based on Ni Cu/ZrO2

| | Catalyst* | | | | | Performance | | | | | | |
|---|---|---|---|---|---|---|---|---|---|---|---|---|
| # | Ni % | Co % | Cu % | Dop. | Dop. % | Time Hours | DEG Conversion GC % | Mor GC % | ADG GC % | MeOEt GC % | MeOAE GC % | Decarbonylation* Σ GC % | Decarbonylation normalized** % |
| 1 | 41.4 | — | 15.2 | Mo | 1.5 | 4 | 59.3 | 18.8 | 29.05 | 0.21 | 0.07 | 0.35 | 0.58% |
| | | | | | | 8 | 76.5 | 32.4 | 26.11 | 0.20 | 0.11 | 0.39 | 0.51% |
| | | | | | | 12 | 93.2 | 50.7 | 14.21 | 0.16 | 0.17 | 0.49 | 0.53% |
| 2 | 40.0 | — | 8.9 | In | 4 | 4 | 57.5 | 17.2 | 28.08 | 0.04 | 0.01 | 0.11 | 0.19% |
| | | | | | | 8 | 96.8 | 60.7 | 20.0 | 0.03 | 0.05 | 0.18 | 0.19% |
| | | | | | | 12 | 99.2 | 68.2 | 3.824 | 0.02 | 0.07 | 0.28 | 0.28% |
| 3 | 44.0 | — | 8.9 | Sb | 3.4 | 8 | 36.5 | 8.3 | 25.4 | 0.06 | 0.02 | 0.13 | 0.35% |
| | | | | | | 10 | 60.2 | 21.2 | 31.73 | 0.08 | 0.04 | 0.19 | 0.31% |
| | | | | | | 12 | 74.7 | 33.7 | 29.34 | 0.09 | 0.07 | 0.25 | 0.34% |

*Catalyst composition in % by weight; remainder up to 100% is ZrO2
**Sum of decarbonylation/DEG conversion
DEG diethylene glycol
Mor morpholine
ADG aminodiglycol
MeOEt methoxyethanol
MeOAE methoxyethylamine
Decarbonylation Sum of methanol, methoxyethanol, methoxyethylamine N-methylmorpholine and methoxyethylmorpholine Workup:

The particular pure products can be obtained from the aqueous crude materials by rectification under reduced pressure, standard pressure or elevated pressure by the known methods. The pure products are obtained either directly in pure form or as azeotropes with water. Aqueous azeotropes can be dewatered by a liquid-liquid extraction with concentrated sodium hydroxide solution before or after the purifying distillation. Distillative dewatering in the presence of an azeotroping agent by known methods is also possible.

In the case that the crude material or the aliphatic amine in the crude material is barely water-miscible, if at all, dewatering is also possible by a separation of the organic and of the aqueous phase by known methods.

The invention claimed is:

1. A process comprising:
   (i) providing a reactant selected from the group consisting of primary alcohols, secondary alcohols, aldehydes, ketones and mixtures thereof; and
   (ii) reacting the reactant with hydrogen and a nitrogen compound selected from the group consisting of ammonia, primary amines, secondary amines and mixtures thereof, in the presence of a catalyst comprising a zirconium dioxide- and nickel-containing catalytically active composition, to form an amine;
   wherein the catalytically active composition, prior to reduction with hydrogen, comprises oxygen compounds of zirconium, copper, and nickel, and one or more oxygen compounds of one or more metals selected from the group consisting of Sb, Pb, Bi, and In.

2. The process according to claim 1, wherein, prior to reduction with hydrogen, the one or more oxygen compounds of the one or more metals selected from the group consisting of Sb, Pb, Bi, and In is present in an amount of 0.1 to 10% by weight, calculated as $Sb_2O_3$, PbO, $Bi_2O_3$, and $In_2O_3$, respectively.

3. The process according to claim 1, wherein, prior to reduction with hydrogen, the one or more oxygen compounds of the one or more metals selected from the group consisting of Sb, Pb, Bi, and In is present in an amount of 0.2 to 7% by weight, calculated as $Sb_2O_3$, PbO, $Bi_2O_3$, and $In_2O_3$, respectively.

4. The process according to claim 1, wherein, prior to reduction with hydrogen, the one or more oxygen compounds of the one or more metals selected from the group consisting of Sb, Pb, Bi, and In is present in an amount of 0.4 to 5% by weight, calculated as $Sb_2O_3$, PbO, $Bi_2O_3$, and $In_2O_3$, respectively.

5. The process according to claim 1, wherein, prior to reduction with hydrogen, the catalytically active composition comprises: 10 to 75% by weight of an oxygen compound of zirconium, calculated as $ZrO_2$; 1 to 30% by weight of an oxygen compound of copper, calculated as CuO; and 10 to 70% by weight of an oxygen compound of nickel, calculated as NiO.

6. The process according to claim 1, wherein, prior to reduction with hydrogen, the catalytically active composition comprises: 25 to 65% by weight of an oxygen compound of zirconium, calculated as $ZrO_2$; 2 to 25% by weight of an oxygen compound of copper, calculated as CuO; and 20 to 60% by weight of an oxygen compound of nickel, calculated as NiO.

7. The process according to claim 1, wherein, prior to reduction with hydrogen, the catalytically active composition comprises: 30 to 55% by weight of an oxygen compound of zirconium, calculated as $ZrO_2$; 5 to 15% by weight of an oxygen compound of copper, calculated as CuO; and 30 to 50% by weight of an oxygen compound of nickel, calculated as NiO.

8. The process according to claim 1, wherein nickel and copper are present in the catalyst in a molar ratio of nickel to copper of greater than 1.

9. The process according to claim 1, wherein the catalytically active composition contains no cobalt.

10. The process according to claim 1, wherein the reaction is carried out at a temperature of 80 to 350° C.

11. The process according to claim 1, wherein the reaction is carried out in liquid phase and at an absolute pressure of 5 to 30 MPa.

12. The process according to claim 1, wherein the reaction is carried out in gas phase and at an absolute pressure of 0.1 to 40 MPa.

13. The process according to claim 1, wherein the reactant is reacted with 0.90 to 100 times the molar amount of the nitrogen compound based on the amount of the reactant.

14. The process according to claim 1, wherein the reactant is reacted with 1.0 to 10 times the molar amount of the nitrogen compound based on the amount of the reactant.

15. The process according to claim 1, wherein the catalyst is present in a fixed bed.

16. The process according to claim 1, wherein the reaction is carried out continuously.

17. The process according to claim 16, wherein the reaction is carried out in a tubular reactor.

18. The process according to claim 16, wherein the reaction is carried out by a cycle gas method.

19. The process according to claim 1, wherein one or both of the reactant and the nitrogen compound is present in the reaction as an aqueous solution.

20. The process according to claim 1, wherein the reactant comprises diethylene glycol, wherein the nitrogen compound comprises ammonia, and wherein the amine comprises monoaminodiglycol and morpholine.

21. The process according to claim 1, wherein the reactant comprises diethylene glycol, wherein the nitrogen compound comprises a mono($C_{1-4}$-alkyl)amine, and wherein the amine comprises N—($C_{1-4}$-alkyl)morpholine.

22. The process according to claim 1, wherein the reactant comprises diethylene glycol, wherein the nitrogen compound comprises a di($C_{1-4}$-alkyl)amine, and wherein the amine comprises one or both of 2-(2-di($C_{1-4}$-alkyl)aminoethoxy) ethanol and bis(2-di($C_{1-4}$-alkyl)aminoethyl)ether.

23. The process according to claim 1, wherein the reactant comprises monoethylene glycol, wherein the nitrogen compound comprises ammonia, and wherein the amine comprises one or both of monoethanolamine and 1,2-ethylenediamine.

24. The process according to claim 1, wherein the reactant comprises monoethanolamine, wherein the nitrogen compound comprises ammonia, and wherein the amine comprises 1,2-ethylenediamine.

25. The process according to claim 1, wherein the reactant comprises a polyether alcohol, wherein the nitrogen compound comprises ammonia, and wherein the amine comprises a polyetheramine corresponding to the polyether alcohol.

26. The process according to claim 1, wherein the reactant comprises N-(2-aminoethyl)ethanolamine, wherein the nitrogen compound comprises ammonia, and wherein the amine comprises one or both of piperazine and diethylenetriamine.

27. The process according to claim 1, wherein the reactant comprises polyisobutenaldehyde, wherein the nitrogen compound comprises ammonia, and wherein the amine comprises polyisobutenamine.

28. A catalytically active composition comprising, prior to reduction with hydrogen: 10 to 75% by weight of an oxygen compound of zirconium, calculated as $ZrO_2$; 1 to 30% by weight of an oxygen compound of copper, calculated as CuO; 10 to 70% by weight of an oxygen compound of nickel, calculated as NiO; and 0.1 to 10% by weight of one or more oxygen compounds of one or more metals selected from the group consisting of Sb, Pb, Bi, and In, calculated as $Sb_2O_3$, PbO, $Bi_2O_3$, and $In_2O_3$, respectively.

29. The catalytically active composition according to claim 28, wherein the one or more oxygen compounds of the one or more metals selected from the group consisting of Sb, Pb, Bi, and In is present in an amount of 0.2 to 7% by weight, calculated as $Sb_2O_3$, PbO, $Bi_2O_3$, and $In_2O_3$, respectively.

30. The catalytically active composition according to claim 28, wherein the one or more oxygen compounds of the one or more metals selected from the group consisting of Sb, Pb, Bi, and In is present in an amount of 0.4 to 5% by weight, calculated as $Sb_2O_3$, PbO, $Bi_2O_3$, and $In_2O_3$, respectively.

31. The catalytically active composition according to claim 28, wherein the oxygen compound of zirconium is present in an amount of 25 to 65% by weight, calculated as $ZrO_2$; wherein the oxygen compound of copper is present in an amount of 2 to 25% by weight, calculated as CuO; and wherein the oxygen compound of nickel is present in an amount of 20 to 60% by weight, calculated as NiO.

32. The catalytically active composition according to claim 28, wherein the oxygen compound of zirconium is present in an amount of 30 to 55% by weight, calculated as $ZrO_2$; wherein the oxygen compound of copper is present in an amount of 5 to 15% by weight, calculated as CuO; and wherein the oxygen compound of nickel is present in an amount of 30 to 50% by weight, calculated as NiO.

33. The catalytically active composition according to claim 28, wherein nickel and copper are present in a molar ratio of nickel to copper of greater than 1.

* * * * *